United States Patent
Sugiura et al.

(10) Patent No.: US 10,345,256 B2
(45) Date of Patent: Jul. 9, 2019

(54) GAS SENSOR

(71) Applicant: DENSO CORPORATION, Kariya, Aichi-pref. (JP)

(72) Inventors: Kei Sugiura, Kariya (JP); Yoshiyasu Ando, Kariya (JP)

(73) Assignee: DENSO CORPORATION, Kariya (JP)

( * ) Notice: Subject to any disclaimer, the term of this patent is extended or adjusted under 35 U.S.C. 154(b) by 196 days.

(21) Appl. No.: 15/509,327

(22) PCT Filed: Sep. 11, 2015

(86) PCT No.: PCT/JP2015/075824
§ 371 (c)(1),
(2) Date: Mar. 7, 2017

(87) PCT Pub. No.: WO2016/043133
PCT Pub. Date: Mar. 24, 2016

(65) Prior Publication Data
US 2017/0261463 A1    Sep. 14, 2017

(30) Foreign Application Priority Data

Sep. 16, 2014  (JP) ................................. 2014-188024
Jul. 29, 2015   (JP) ................................. 2015-149660

(51) Int. Cl.
 G01N 27/407  (2006.01)
 G01N 27/41   (2006.01)
 G01N 33/00   (2006.01)

(52) U.S. Cl.
 CPC ..... *G01N 27/4074* (2013.01); *G01N 27/4071* (2013.01); *G01N 27/4072* (2013.01);
(Continued)

(58) Field of Classification Search
 CPC ..... G01N 27/406–4074; G01N 27/409; G01N 27/41; G01N 33/0037; Y02A 50/245
 See application file for complete search history.

(56) References Cited

U.S. PATENT DOCUMENTS

2008/0190767 A1* 8/2008 Nakae ................ G01N 27/4071
                                                              204/424
2012/0247957 A1* 10/2012 Murakami ......... G01N 27/4067
                                                              204/408

(Continued)

FOREIGN PATENT DOCUMENTS

JP          11-83793          3/1999
JP        2000097903 A   *  4/2000
(Continued)

*Primary Examiner* — Maris R Kessel
(74) *Attorney, Agent, or Firm* — Nixon & Vanderhye P.C.

(57) ABSTRACT

In a gas sensor where an exhaust gas is introduced into a chamber provided in a gas sensor element so that an oxygen concentration is reduced in a pump cell on the upstream side to detect $NO_x$ in the exhaust gas in a sensor cell on the downstream side, the surface of at least one of a solid electrolyte sheet and a shielding sheet that constitute wall surfaces of the chamber has a warped shape which is convex inwardly of the chamber at a position where the pump cell is formed. The warp amount is in the range from 0.10% or higher to 1.38% or lower, and the height in the stacking direction of the diffusion layer is lower than the average height Have in the stacking direction of the chamber at the position where the pump cell is formed.

8 Claims, 11 Drawing Sheets

(52) U.S. Cl.
CPC ......... *G01N 27/41* (2013.01); *G01N 33/0037* (2013.01); *Y02A 50/245* (2018.01)

(56) References Cited

U.S. PATENT DOCUMENTS

2014/0353155 A1* 12/2014 Oya ................... G01N 27/4071
 204/424
2015/0226696 A1* 8/2015 Satou ................. G01N 27/4067
 204/426

FOREIGN PATENT DOCUMENTS

| JP | 2010-261727 | | 11/2010 | | |
|----|----|----|----|----|----|
| JP | 2011043333 A | * | 3/2011 | ......... | G01N 27/4067 |
| JP | 2013-117428 | | 6/2013 | | |

* cited by examiner

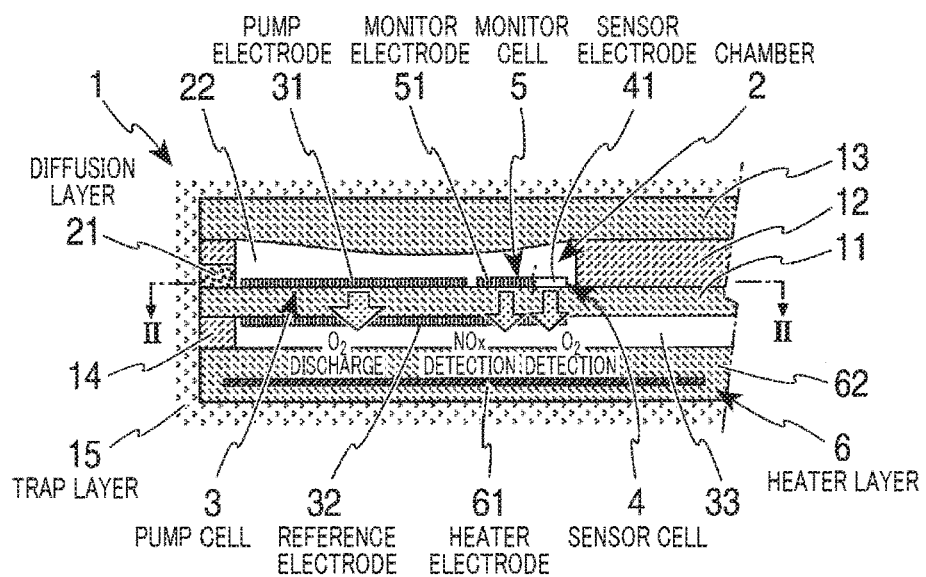
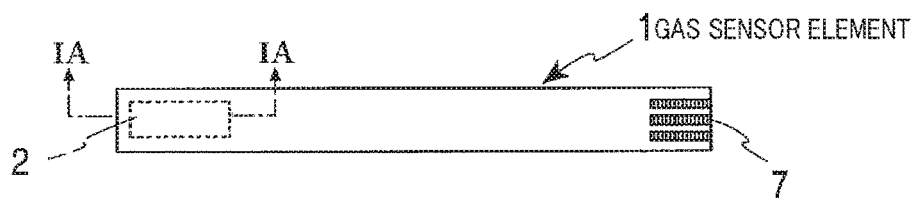
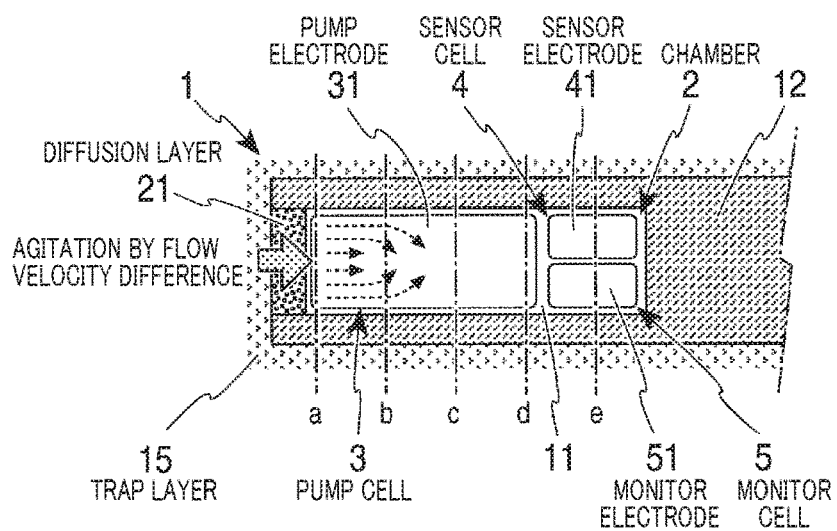

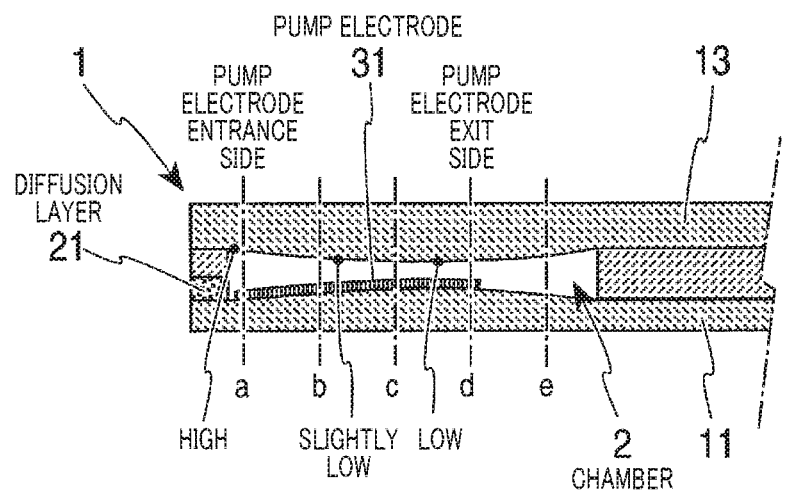
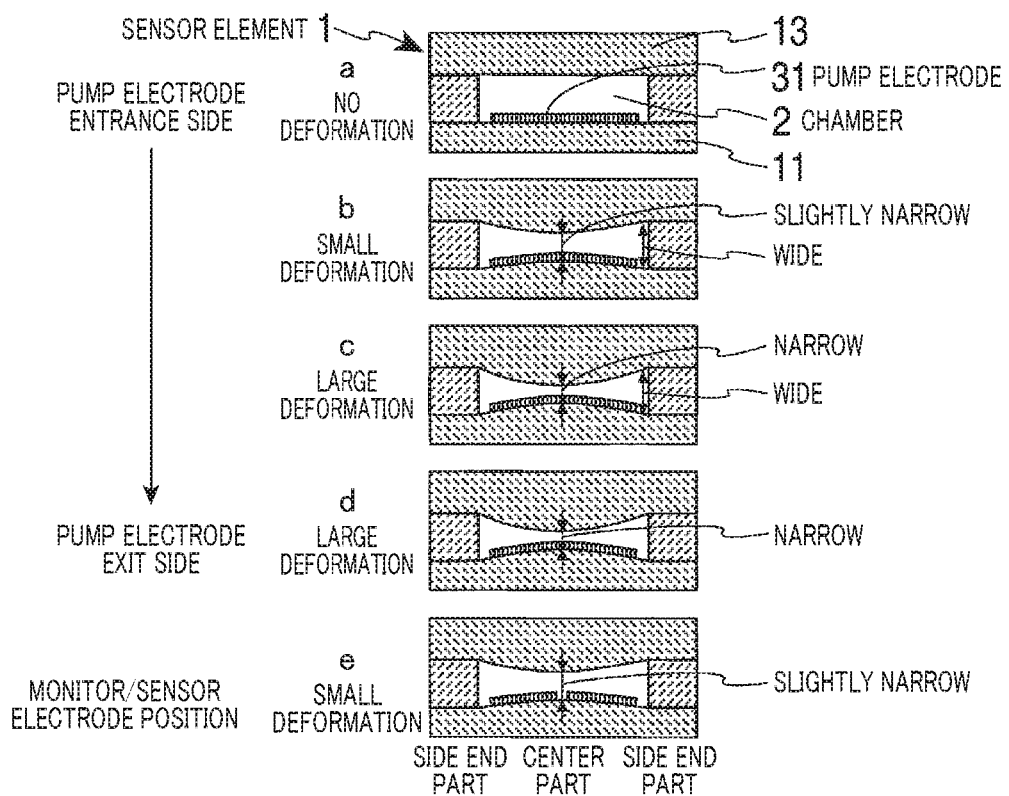

FIG.7A
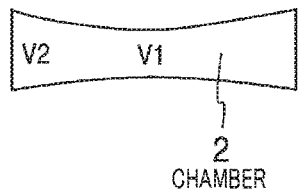
CHAMBER TRANSVERSE DIRECTION
GENERAL EXPRESSION OF GAS FLOW RATE Q
$Q = C \times \Delta p$
(C: GAS FLOW RATE COEFFICIENT,
$\Delta p$: DIFFERENTIAL PRESSURE)
2 CHAMBER
FIG.7B
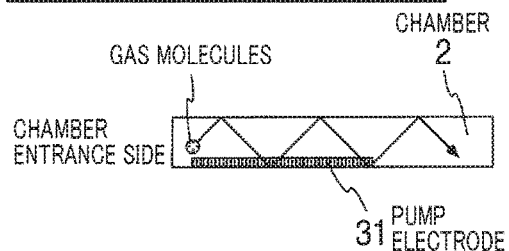
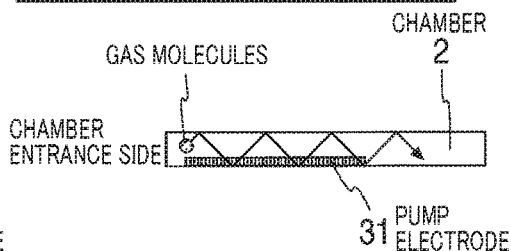
LOW COLLISION FREQUENCY (LOW DISCHARGING CAPACITY)
HIGH GAS FLOW RATE (HIGH DETECTION ACCURACY)
HIGH COLLISION FREQUENCY (HIGH DISCHARGING CAPACITY)
LOW GAS FLOW RATE (LOW DETECTION ACCURACY)
FIG.8
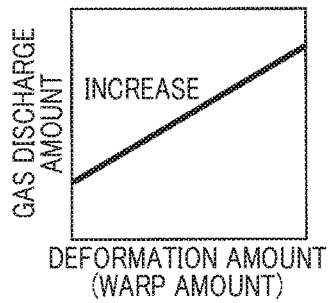
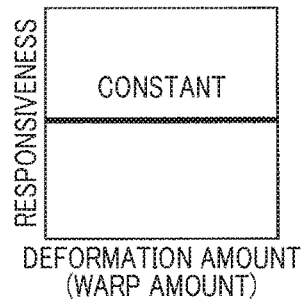
FIG.9
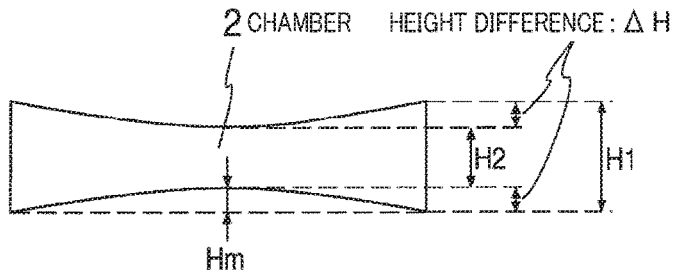

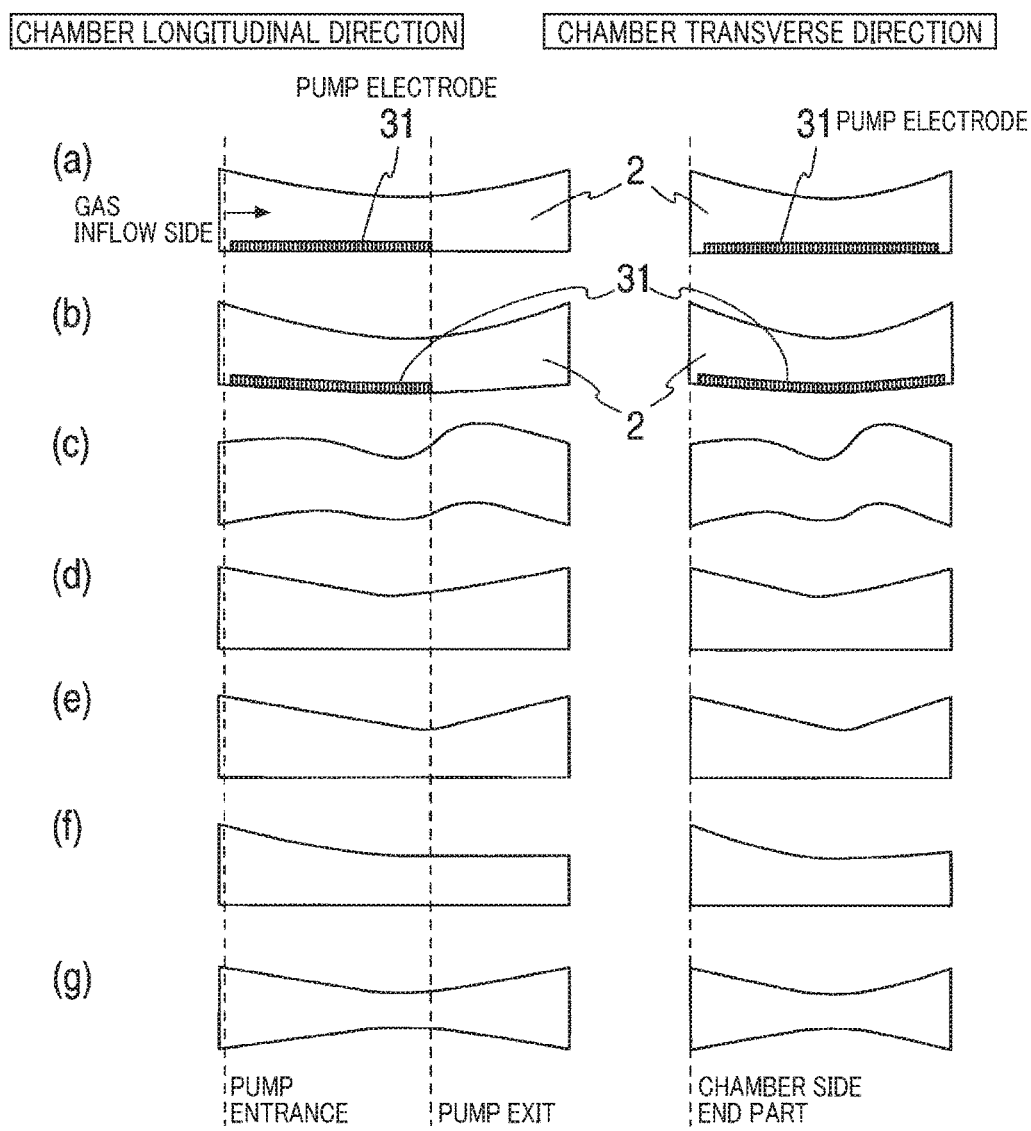

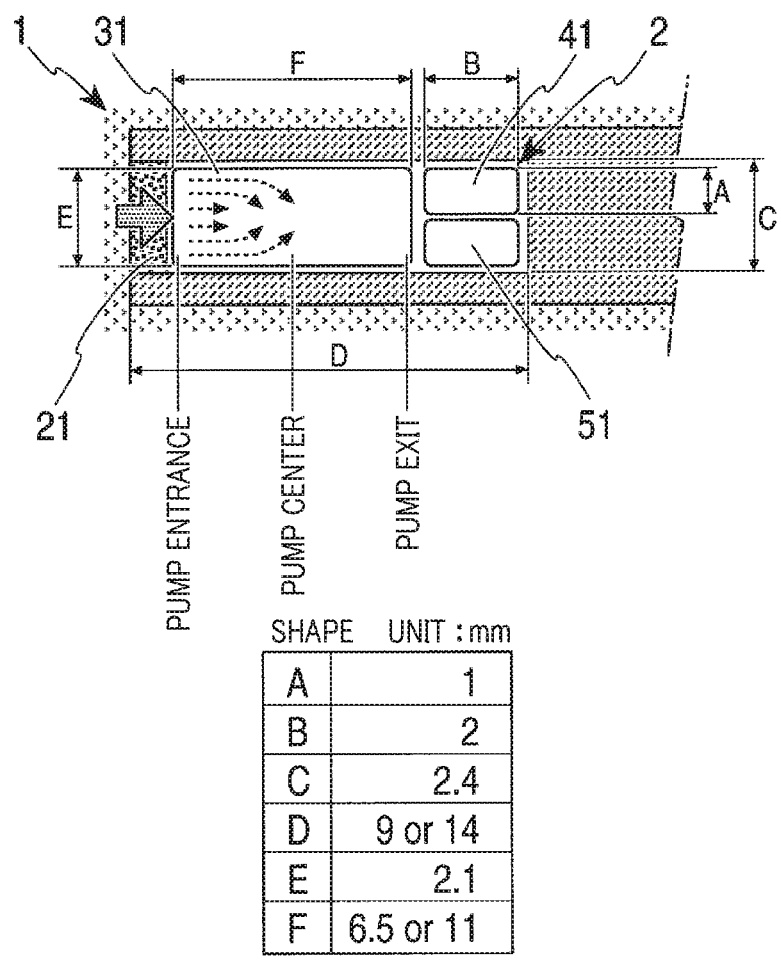

GAS SENSOR

This application is the U.S. national phase of International Application No. PCT/JP2015/075824 filed Sep. 11, 2015 which designated the U.S. and claims priority to JP Patent Application No. 2014-188024 filed Sep. 16, 2014, and JP Patent Application No. JP 2015-149660 filed Jul. 29, 2015, the entire contents of each of which are hereby incorporated by reference.

TECHNICAL FIELD

The present invention relates to a gas sensor for detecting a specific gas component such as nitrogen oxide ($NO_x$) contained in exhaust gas of an internal combustion engine, and more specifically, a chamber formed in a stacked-type sensor element.

BACKGROUND ART

Generally, a gas sensor used for an exhaust gas purification system of an internal combustion engine includes a chamber into which exhaust gas containing $NO_x$ is introduced, a pump cell disposed on the upstream side within the chamber for pumping out oxygen in the exhaust gas from the chamber, and a sensor cell disposed on the downstream side within the chamber for detecting a $NO_x$ concentration in the exhaust gas whose oxygen concentration has been reduced. The pump cell and the sensor cell of the gas sensor are formed such that a pair of electrodes are formed in a solid electrolyte sheet having oxygen ion conductivity and constituting a chamber wall, and a sensor element is formed by stacking a heater sheet and an insulating sheet on the solid electrolyte sheet. Other than the gas sensor of such 2-cell structure, there is known a gas sensor of a three-cell structure in which a sensor cell and a monitor cell are disposed side by side on the downstream side of a chamber to monitor the oxygen concentration in the chamber (for example, refer to patent literature 1 and so on).

Patent literature 1 describes a principle of detection of $NO_x$ by a gas sensor, in which exhaust gas is introduced into a chamber as an inner space of a stacked-type sensor element, and oxygen that obstructs detection is discharged to the outside from the chamber while the exhaust gas passes through the pump cell on the upstream side. At this time, when a voltage applied to the pump cell is set such that the current value of a current flowing by the oxygen within the chamber does not depend on the voltage value, it operates as a limiting current-type oxygen sensor. Thereafter, $NO_x$ in the exhaust gas whose oxygen concentration has been reduced is decomposed in the sensor cell on the downstream side, so that the $NO_x$ concentration can be detected from the value of a current that occurs at that time. Further, by providing the monitor cell to detect a remaining oxygen concentration in the exhaust gas that has reached the sensor cell, the voltage applied to the pump cell can be feed-back controlled.

Incidentally, the gas sensor of the two-cell or three-cell structure is known as an oxygen sensor (for example, see patent literature 2 and so on).

PRIOR ART LITERATURE

Patent Literature

[PTL1] Japanese Patent Application Laid-open No. H11-83793
[PTL2] Japanese Patent Application Laid-open No. 2013-117428

SUMMARY OF THE INVENTION

Technical Problem

The properties which a gas sensor requires include accuracy and responsiveness of $NO_x$ detection. To increase the accuracy of $NO_x$ detection, it is desirable to increase the frequency that an exhaust gas passing through a pump cell contacts an electrode of the pump cell for sufficiently discharging oxygen gas so that the gas whose oxygen concentration has been sufficiently discharged can be sent to a sensor cell. Further, to increase the responsiveness of $NO_x$ detection, it is necessary to satisfactory disperse the gas taken into the chamber, to thereby cause the exhaust gas to reach the sensor cell rapidly.

However, these two required properties are contradictive to each other, and it is difficult to achieve both of them. That is, a structure in which the exhaust gas easily accumulates on the electrode of the pump cell is preferable to sufficiently discharge the oxygen gas, however, since the time required for the exhaust gas pass through the pump cell becomes long, the gas is prevented from dispersing satisfactorily.

The present invention has been made in view of such problem with an object of providing a high-performance gas sensor improved in both the $NO_x$ detection accuracy and the responsiveness by effectively diffusing exhaust gas within the chamber while efficiently discharging oxygen in the exhaust gas.

Solution to Problem

One aspect of the invention is in a gas sensor for detecting a specific component in a measurement gas, including:

a chamber that is provided in a gas sensor element comprised of stacked tabular ceramic sheets, the measurement gas being introduced into the chamber through a porous diffusion layer provided at an end part thereof in a longitudinal direction of the gas sensor element;

a pump cell that has a pump electrode disposed on an upstream side of a gas flow within the chamber for pumping out oxygen in the measurement gas; and a sensor cell that has a sensor electrode disposed on a downstream side of the gas flow within the chamber for detecting a concentration of a specific gas in the measurement gas whose oxygen concentration has been reduced, wherein the gas sensor element has a structure in which a first ceramic sheet on whose surface facing the chamber the pump electrode and the sensor electrode are disposed, a second ceramic sheet having an opening to make the chamber, and a third ceramic sheet covering the opening to define the chamber are stacked on one another, the chamber has a warp shape in which a surface of at least one of the first ceramic sheet and the third ceramic sheet constituting a chamber wall is convex inwardly of the chamber at a position where the pump cell is formed, a warp amount of the surface being set in a range from 0.1% or higher to 1.38% or lower, and the diffusion layer and the chamber satisfy a relationship of Hp<Have, where Hp is a height of the diffusion layer in a stacking direction and Have is an average height of the chamber in a stacking direction at the position where the pump cell is formed.

Advantageous Effects of Invention

Since the surface of at least one of the two ceramic sheets facing the chamber provided in the stacked-type gas sensor element and constituting its inner surface has a warp shape, the in-chamber space has such a shape that it is narrow at the pump cell position located on the upstream side in the gas flow direction than on the entrance side. Accordingly, since there occurs a gas flow heading from the side end part to the pump cell center part, a gas flow-agitating effect can be obtained. Further, since the height Hp of the porous diffusion layer through which gas is introduced from the outside is set lower than the chamber average height Have at the pump cell position, the amount of the gas introduced into the in-chamber space can be reduced to thereby increase the gas diffusibility at the chamber entrance part. Accordingly, it is possible to increase the capability of pumping oxygen toward the exit side while drawing a sufficient amount of the measurement gas on the entrance side of the pump cell.

As a result, since the frequency that the exhaust gas contacts the pump electrode increases significantly to promote discharging of oxygen by the pump electrode, the measurement gas is further drawn from the space at the side end part into the pump cell. Accordingly, it is possible to efficiently remove oxygen to sufficiently reduce the oxygen concentration of the measurement gas introduced into the sensor cell. At this time, since the warp amount of the surface making the chamber wall is in the range from 0.1% or higher to 1.38% or lower, it is possible to prevent occurrence of cracks in a sintering/degreasing step and a sheet stacking/compressing step to increase reliability. Hence, according to the above described aspect, since both of a favorable gas dischargibility and a favorable gas diffusibility can be achieved, it is possible to increase the detection accuracy of specific gas by the sensor cell and ensure responsiveness to implement a high-performance gas sensor.

BRIEF DESCRIPTION OF THE DRAWINGS

FIG. 1A is a diagram showing a distal end structure of a gas sensor element constituting a gas sensor of a first embodiment, which is a IA-IA line cross-sectional view of FIG. 1B;

FIG. 1B is a schematic overall structure diagram of the gas sensor element constituting the gas sensor of the first embodiment of the present invention;

FIG. 2 is a diagram showing a planar structure of the distal end part of the gas sensor element, which is a II-II line cross-sectional view of FIG. 1;

FIG. 5 is a longitudinal cross-sectional view schematically showing a chamber structure which is a main part of a gas sensor element of a second embodiment;

FIG. 6 is a transverse cross-sectional view schematically showing the chamber structure which is the main part of the gas sensor element of the second embodiment;

FIG. 7A is a schematic transverse cross-sectional diagram for explaining a gas flow within a chamber;

FIG. 7B is a schematic longitudinal cross-sectional diagram for explaining the gas flow within the chamber comparing with respect to the chamber height;

FIG. 8 is a diagram showing a relationship between a chamber deformation amount and a sensor characteristic;

FIG. 9 is a schematic cross-sectional diagram for explaining a relationship between the sensor characteristic and a chamber shape;

FIG. 10 is a schematic cross-sectional diagram showing examples of the chamber shape in the longitudinal and transverse directions.

FIG. 16 is a plan diagram showing an example of shape of the gas sensor element in practical examples;

DESCRIPTION OF EMBODIMENTS

First Embodiment

Figure 3:
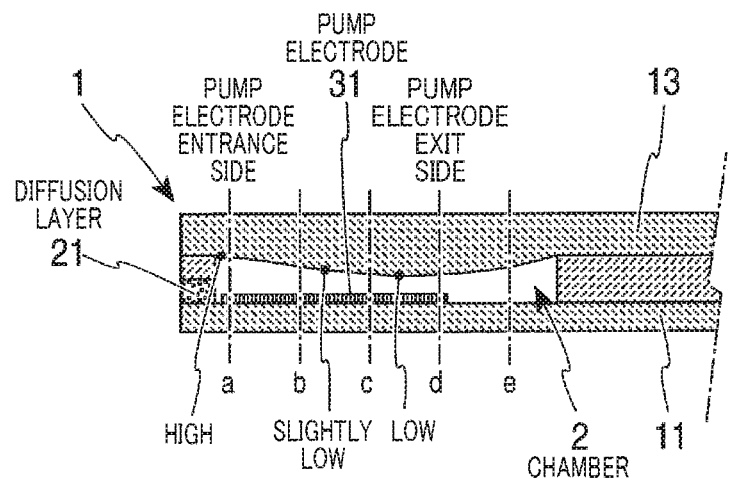
FIG. 3 is a longitudinal cross-sectional view schematically showing a chamber structure which is a main part of the gas sensor element.

A first embodiment of a gas sensor is explained in detail in the following with reference to the drawings. For example, the gas sensor of this embodiment is installed as a $NO_x$ sensor in an exhaust passage of an internal combustion engine to detect nitrogen oxide (namely, $NO_x$) as a specific gas component contained in an exhaust gas as a measurement gas. FIG. 1B shows a gas sensor element 1 constituting the gas sensor. FIG. 1A shows a cross-section of the element distal end part (that is, the left-most end part in the drawing). Exhaust gas is introduced into a chamber 2 which is a space provided as a main part in the element through a porous diffusion layer 21. As shown in FIG. 2, within the chamber 2, a pump cell 3 is disposed on the distal end side (that is, on the left end side in the drawing) which is the upstream side of a gas flow. A sensor cell 4 and a monitor cell 5 are disposed on the proximal end side (that is, on the right end side in the drawing) which is the downstream side of the gas flow.

Figure 4:
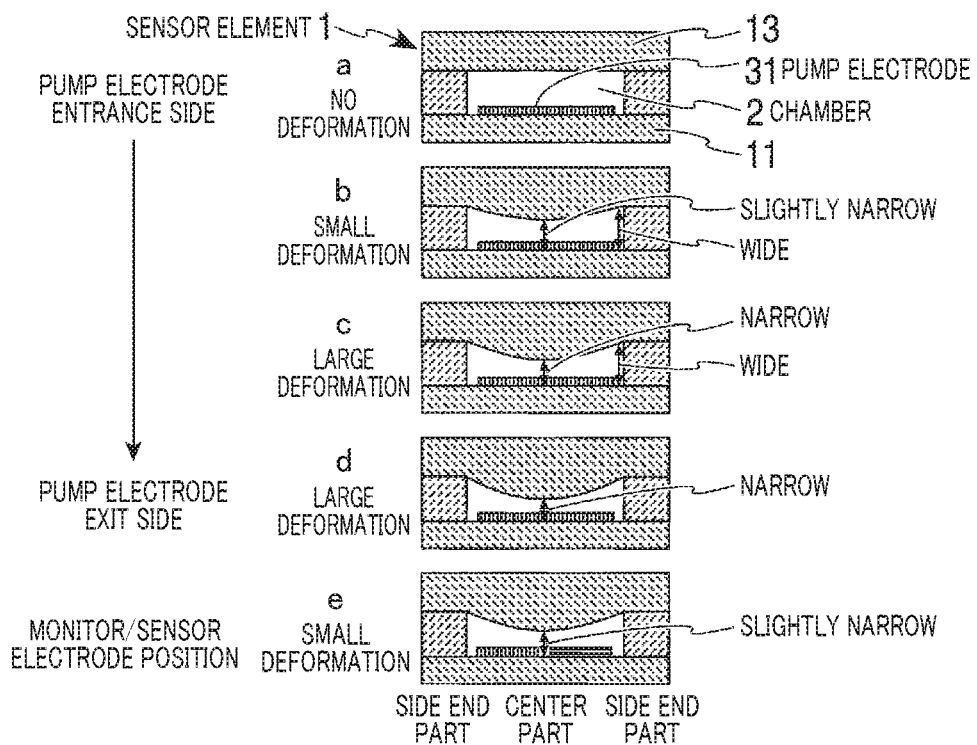
FIG. 4 is a transverse cross-sectional view schematically showing the chamber structure which is the main part of the gas sensor element.

The gas sensor 1 has a chamber structure in which there is no partition in the chamber 2. The diffusion layer 21 is located so as to close the opening on the upstream side of the chamber 2 at the distal end part in the element longitudinal direction. The chamber 2 has a shape to achieve satisfactory gas diffusibilty, in which a part of the inner surface constituting the chamber wall is warped so that the chamber height varies from the upstream side to the downstream side of the gas flow to thereby promote the oxygen ($O_2$) pumping function of the pump cell 3. Each of cells 3 to 5 are connected to a not-shown electrode terminal formed on the proximal end part through not-shown lead wires. Examples of the longitudinal and transverse cross-sectional shapes of the chamber 2 which are schematically shown in FIGS. 3 and 4 are described later in detail.

In FIG. 1A, the gas sensor element 1 is comprised of a stacked body which is formed of long and narrow plate-like ceramic sheets stacked in the plate thickness direction. More specifically, it has a basic structure in which, on the upper surface of a solid electrolyte sheet 11 as a first ceramic sheet, a chamber forming sheet 12 as a second ceramic sheet and a shielding sheet 13 as a third ceramic sheet are stacked in succession. The chamber forming sheet 12 is punch-formed with a rectangular opening 22 that makes the chamber 2. On the bottom surface of the solid electrolyte sheet 11, a heater layer 6 is stacked through a duct forming layer 14 as a fourth ceramic sheet. The duct forming layer 14 is formed with a duct 33 comprised of an opening that leads to a not-shown proximal end part to introduce atmospheric air as a reference gas from the outside. The heater layer 6 has a structure in which a heater electrode 61 is embedded in a heater sheet 62 as a fifth ceramic sheet. The first to fifth ceramic sheets are made of insulation sheets having no permeability to the measurement gas.

The gas sensor element 1 is covered with a porous layer as a trap layer 15 at its whole outer surface. The trap layer 15 traps moisture and poisoning components contained in the exhaust gas to prevent them from entering the chamber 2 to thereby protect the gas sensor element 1. Incidentally, the respective cells 3, 4 and 5 and the heater layer 6 in the gas sensor element 1 are connected to a terminal part 7 (for example, see FIG. 1B) through not-shown lead wires to be connected to an external drive control unit including a gas detection means, an energization means and so on. The heater layer 6 generates heat by being energized to heat the respective cells 3, 4 and 5 to a temperature appropriate for gas detection.

The pump cell 3 is comprised of the solid electrolyte sheet 11, pump electrodes 31 as a pair of electrodes formed at opposite positions on both surfaces of the solid electrolyte sheet 11, and a reference electrode 32. The solid electrolyte sheet 11 is a sheet made of a solid electrolyte body having oxygen ion conductivity such as partially stabilized zirconia. Porous cermet electrodes are used as the pump electrodes 31 and the reference electrode 32. Preferably, the pump electrode 31 is an electrode which is low in $NO_x$ degrading activity, for example, a porous cermet electrode containing Pt (platinum) and Au (gold) to suppress degradation of $NO_x$ contained in the exhaust gas. By applying a predetermined voltage to the paired electrodes, $O_2$ gas contained in the exhaust gas reaching the pump electrode 31 is degraded, transmits through the solid electrolyte sheet 11 and is discharged to the reference electrode 32. By this pumping action, it is possible to discharge $O_2$ gas from the pump electrode 31 facing the chamber 2 to the reference electrode 32 facing the duct 33 to thereby reduce the $O_2$ concentration of the exhaust gas passing through the pump cell 3.

The sensor cell 4 is comprised of the solid electrolyte sheet 11, sensor electrodes 41 as paired electrodes formed at opposite positions on both surfaces of the solid electrolyte sheet 11, and the reference electrode 32. The monitor cell 4 is comprised of the solid electrolyte sheet 11, monitor electrodes 51 as paired electrodes formed at opposite positions on both surfaces of the solid electrolyte sheet 11, and the reference electrode 32. Preferably, porous cermet electrodes whose principal component are noble metal are used as the sensor electrodes 41 and the monitor electrodes 51. Preferably, the sensor electrode 41 is an electrode which is high in degrading activity to $NO_x$ in the exhaust gas, for example, a porous cermet electrode containing Pt and Rh (rhodium), and the monitor electrode 51 is an electrode which is low in NOx degrading activity, for example, a porous cermet electrode containing Pt and Au. The reference electrode 32 is provided as a common electrode for the pump cell 3, the sensor cell 4, the monitor cell 5 on the surface of the solid electrolyte sheet 11 opposite to the surface that defines the chamber 2 so as to be opposed to all of the pump electrodes 31, the sensor electrode 41 and the monitor electrode 51. As the reference electrode 32, a porous cermet electrode whose principal component is Pt is used, for example.

NOx gas in the exhaust gas reaching the sensor cell 4 is degraded on the sensor electrode 41, and occurring oxygen ions transmit through the solid electrolyte sheet 11 and are discharged to the reference electrode 32. A current flowing at that time is detected as the concentration of NOx contained in the exhaust gas. On the other hand, in the monitor cell 5, $O_2$ gas reaching above the monitor electrode 51 is degraded and discharged to the reference electrode 32. A current flowing at that time is detected as the concentration of remaining oxygen in the exhaust gas. The monitor cell 5 is located at the position equivalent to the sensor cell 4 in the gals flow direction within the chamber 2, and accordingly it is possible to effectively feed-back control the pump cell 3 by monitoring the remaining oxygen concentration.

In FIG. 2, the chamber 2 has a rectangular shape in which the length of the gas sensor element 1 in the longitudinal direction (that is, the chamber length) is longer than the length in the transverse length (that is, the chamber width). The diffusion layer 21 formed of a porous body whose width is the same as the chamber width is disposed at the entrance part of the chamber 2 along the longitudinal direction in a predetermined thickness so as to transverse the entrance part to separate it from the outer space, to introduce the exhaust gas into the inside at a predetermined diffusion resistance. Within the chamber 2, the pump electrode 31 located on the upstream side of the gas flow is formed in a roughly rectangular shape whose width is slightly smaller than the chamber width between the diffusion layer 21 and the sensor electrode 41 and monitor electrode 51 which are located at the downstream end part. The sensor electrode 41 and the monitor electrode 51 have roughly the same rectangular shape whose width is slightly smaller than half of the chamber width.

The pump electrode 3 has a sufficiently large area compared to the sensor electrode 41 and the monitor electrode 51 to effectively discharge $O_2$ gas in the introduced exhaust gas. Preferably, the length in the gas flow direction of the pump electrode 31 is set 2 to 4 times, for example, 3 times that of the sensor electrode 41 and the monitor electrode 51 to enable sufficient contact with the exhaust gas. To discharge $O_2$ gas in the exhaust gas reliably, it is preferable that the pump electrode 31 is large, however, on the other hand, since it takes a time for $O_2$ gas to pass through the pump cell 31, the responsiveness is lowered. Further, there is a concern that $O_2$ gas in the exhaust gas may pass through without being discharged along the side end part of the chamber 2 where the pump electrode 31 is not formed.

Accordingly, as shown in FIG. 1A, a part of the wall surface of the chamber 2 in the stacking direction of the gas sensor element is deformed to enable controlling the gas flow within the chamber 2, and the height of the diffusion layer 21 disposed at the entrance part of the chamber 2 is set lower than the height of the wall surface of the chamber 2 to restrict an amount of the exhaust gas being introduced. Specifically, the surface of at least one of the shielding sheet 13 and the solid electrolyte sheet 11 which are opposite to each other across the chamber 2 is made a warped surface having a warped shape which is convex toward the inside of the chamber 2 at the position where the pump cell 3 is formed. Accordingly, since the height in the stacking direction of the chamber 2 varies in the longitudinal direction and the transverse direction of the gas sensor element 1, the introduced gas is agitated due to flow velocity difference, and as a result, a flow toward the pump cell is created (see FIG. 2, for example).

The warp amount of this warped surface is set in a range from 0.1% or higher to 1.38% or lower. The warp amount represents a deformation rate of a warped surface with respect to a non-warped reference surface. Here, the warp amount is determined based on a maximum deformation amounts in the longitudinal and transverse cross sections of the gas sensor element 1. If the warp amount is less than 0.10%, there is a concern that there may occur cracks during a sintering/degreasing step of a manufacturing process of the gas sensor element 1. The velocity difference increases with the increase of the warp amount, however, there is a concern that there may occur cracks during a sheet stacking/compressing step.

The diffusion layer 21 and the chamber 2 satisfy the relationship of Hp<Have, where Hp is the height in the stacking direction of the diffusion layer 21, and Have is the average height in the stacking direction of the chamber 2 at the position where the pump cell 3 is formed. Accordingly, the exhaust gas that has passed through the porous diffusion layer 21 is caused to diffuse into the wider inner space of the chamber 2. The average height Have of the chamber 2 is calculated based on the averaged value of chamber heights in the longitudinal cross section of the gas sensor element 1 at a plurality of points from the entrance side to the exit side of the pump cell 3.

The diffusion layer 21 is formed by embedding a porous sheet in the distal end of the chamber forming sheet 12 that forms the chamber 2, for example. The height Hp of the diffusion layer 21 is lower than the height of the chamber forming sheet 2 (that is, the sheet thickness). As shown in the drawing, the position of the diffusion layer 21 relative to the chamber forming sheet 12 may be, other than a position facing the solid electrolyte sheet 11, either a position facing the shielding sheet 13 or an intermediate position in the stacking direction.

Preferably, as schematically shown in FIGS. 3 and 4, the shape is such that the cross-sectional area at the downstream end part of the pump electrode 31 (that is, the gas exit part) is smaller than at the upstream end part (that is, the gas entrance part) in the longitudinal direction of the gas sensor element 1 or the gas flow direction, and that the height at the intermediate part where the pump cell 3 is formed, particularly at the position of the center part of the pump electrode 31, is lower than the height of at least one of the wall surfaces of the side end part in the transverse direction. In this embodiment, the shielding sheet 13 located on the opposite side of the pump electrode 31 and forming the wall of the chamber 2 is deformed. The surface of the shielding sheet 13 exposed to the chamber 2 (that is, the lower surface in FIG. 3) is made in a warped shape which is convex toward the inside of the chamber 2.

This warped shape is preferably formed on a warped surface of a chevron curved shape which is smoothly curved such that the deformation becomes maximum, or the chamber height becomes low at downstream from the center part of the pimp electrode 31. In this embodiment, the height of the chamber 2 gradually decreases from an entrance part a on the entrance side toward an exit part don the exit side of the pump electrode 31 so that the cross sectional area gradually decreases. Between the entrance part a and the exit part d, the height of the chamber 2 becomes lower at an intermediate part c downstream from the center part of the pump electrode 31 than at an intermediate part b on the upstream side. The height of the exit part d and the height of the intermediate part c upstream of the exit part d are approximately equal to each other. Preferably, the heights of the respective parts along the longitudinal direction satisfy the relationship of entrance height Ha>Hb>Hc≥exit height Hd. The height of the pump electrode 31 at the downstream side e (that is, at the position where the sensor electrode 41 and the monitor electrode 51 are formed) is slightly higher that at the exit part d. The height of the chamber 2 gradually increases from the exit part d at which it is minimum. Specifically, it may be comparable to the height between the entrance part a and the intermediate part c on the downstream side. For example, it may be comparable to the intermediate part b on the upstream side.

FIG. 4, which is a transverse cross-sectional diagram, shows specific cross-sectional shapes corresponding to the respective parts a to e of FIG. 3. The chamber 2 has a roughly rectangular cross-sectional shape at the entrance part a of the pump electrode 31. The shielding sheet 13 that makes the chamber wall 2 on the opposite side of the pump electrode 31 has little deformation. A sufficient amount of the exhaust gas is introduced into the entrance part a through the diffusion layer 21. In the respective parts b toe downstream therefrom, the surface of the shielding sheet 13 exposed to the chamber 2 has a warped shape which is convex toward the inside of the chamber 2, here, a chevron curved shape which is curved such that the deformation becomes maximum at the center part, and the center part space within the chamber 2 is narrow. This deformation amount gradually increases toward the exit part d of the pump electrode 31 so that the cross-sectional area gradually decreases. The deformation amount of the pump electrode 31 at the downstream part e is slightly larger than at the exit part d, while the cross-sectional area is slightly larger.

The cross-sectional shapes of the respective parts b to e are such that the wall height is constant and the space is entirely wide in both side end parts, while, in the intermediate part, the height of the chamber 2 gradually decreases toward the center part of the pump electrode 31 and the space becomes narrower toward the center part. The cross-sectional areas satisfy the relationship of entrance part a>b>c≥exit part d. The cross-sectional area on the downstream side E is between those of the entrance part a and the intermediate part c on the downstream side, for example, comparable to that of the intermediate part b on the upstream side. Since the intermediate part is narrow, the $O_2$ pumping capacity increases, and the gas diffusibility can be ensured at both the wide side end parts. Further, since the velocity difference between both side end parts and the center part increases, the gas flow is agitated to enable efficient discharging of $O_2$.

Second Embodiment

As shown as a second embodiment in FIGS. 5 and 6, both the wall surfaces of the chamber 2 which are opposite to each other in the stacking direction of the gas sensor element 1 may be deformed. In this embodiment, the relationship between the average height Have of the chamber 2 at the position where the pump cell 3 is formed and the shape or disposition of the not-shown diffusion layer 21 is the same as that in the first embodiment, and accordingly, the following explanation is given with a focus on differences therebetween. Specifically, the solid electrolyte sheet 11 formed with the shielding sheet 13 and the pump electrodes 31 is formed such that the surface exposed to the chamber 2 has a warped shape which is convex toward the inside of the chamber 2 in the longitudinal direction (see FIG. 5, for example), so as to be a chevron curved shape in which the height of the chamber gradually decreases form the entrance part a toward the exit part d of the pump electrode 31 and the warp amount becomes maximum at the gas exit part. Like the first embodiment, it is preferable that the exit part d and the height upstream therefrom are in the relation of entrance height Ha>Hb>Hc≥exit height Hd. For example, the cross-sectional area becomes maximum at the gas entrance part and becomes minimum at the gas exit part of the pump electrode 31. The height at the downstream side E (the position where the sensor electrode 41 and the monitor electrode 51 are formed) may be comparable to the height between the entrance part a and the intermediate part c on the downstream side. For example, it may be comparable to the intermediate part b on the upstream side.

The transverse cross sections of FIG. 6 correspond to the cross sections of the respective parts a to e of FIG. 5. Like the first embodiment, the chamber 2 has a roughly rectangular cross-sectional shape at the entrance part a of the pump electrode 31, and the shielding sheet 13 and the solid electrolyte sheet 11 making the wall of the chamber 2 have little deformation. In the respective parts a to e downstream therefrom, the surfaces of the solid electrolyte sheet 11 and the shielding sheet exposed to the chamber 2 have a warped shape which is convex toward the inside of the chamber 2, here, a chevron curved shape which is curved such that the deformation becomes maximum at the center part. This deformation amount gradually increases toward the exit part d of the pump electrode 31, and accordingly the deformation amount of the pump electrode 31 is slightly smaller on the downstream side e than on the exit side d. The respective parts b to e have a cross-sectional shape in which the deformation amount is small compared to the intermediate part, the wall height is constant and the space is entirely wide, the space is narrow at the intermediate part, and the height of the chamber 2 gradually decreases toward the center part. The cross-sectional areas satisfy the relationship of entrance part a>b>c≥exit part d. The cross-sectional area on the downstream side e is between those of the entrance part a and the intermediate part c, for example, comparable to that of the upstream part b.

The warp amount of the warped surface exposed to the chamber 2 is set in a range from 0.1% or higher to 1.38% or lower in the shielding sheet 13 and the solid electrolyte sheet 11. The warped shape and the warp amount of each of the shielding sheet 13 and the solid electrolyte sheet 11 may be set appropriately as long as the relationship of the height Hp in the stacking direction of the diffusion layer 21<the average height Have in the stacking direction of the chamber 2 at the position where the pump cell 3 is formed is satisfied to obtain a desired property.

As explained above, the shape of the chamber 2 in the first or second embodiment enables gas drawing as well as in prior art by appropriately setting the average height Have at the position where the pump cell 3 is formed with respect to the height Hp of the diffusion layer 21, and making one of or both of the opposite surfaces in the stacking direction to ensure a cross-sectional area on the entrance side end part of the pump electrode 31. In addition, since the deformation amount of the wall surface increases and the cross-sectional area decreases from the entrance side toward the exit side end part, $O_2$ discharging by the pump electrode 31 is promoted to increase the pumping capacity. Further, since the cross-sectional shape is such that it is narrower at the intermediate part and wider at both side end parts on the downstream side of the entrance side end part, there occurs a velocity difference in the flow of the gas introduced from the entrance side as shown in FIG. 2, the gas flow is agitated at the side end parts while increasing the gas diffusibility by the velocity difference with the center part. As a result, $O_2$ discharging by the pump electrode 31 can be further promoted while ensuring the responsiveness. The advantageous effects of the present invention are explained with reference to FIGS. 7 to 9.

FIG. 7A schematically shows a typical shape in the transverse direction of the chamber 2 of the second embodiment, where the volume of the center part at which the distance of the opposed wall surfaces within the chamber 2 becomes minimum is V1, and the volume of the side end part at which the distance becomes maximum is V2. When a differential pressure between the center part and the side end part is ΔP, a gas flow rate Q is given by the following general expression.

The general expression of the gas flow rate Q=C×Δp, where C is a coefficient representing gas flowability.

Here,
from gas state equation of PV=nRT,
Differential Pressure $$\Delta P = P1 - P2$$
$$= nRT \times (1/V1 - 1/V2)$$
$$= nRT \times \{(V2 - V1)/V1 \cdot V2\},$$

where P1: pressure of the center part, P2: pressure of the side end part, R: gas constant, and T: temperature.

Accordingly, the flow rate Q of the gas increases in proportion to the differential pressure Δp, and the gas flows more easily with the increase of the difference in volume between the side end part and the center part.

FIG. 7A, which schematically shows a relationship between the height in the longitudinal direction of the chamber 2 and the gas flow, and compares a case where the chamber height is higher (that is, the left figure) with a case where it is lower (that is, the right figure). If the chamber height is constant in the longitudinal direction, when the exhaust gas is introduced into the chamber 2 from the entrance side on the left side of the figure, gas molecules including $O_2$ move to the downstream side while hitting the wall surfaces of the chamber 2. As apparent from the figures, the case where the chamber height is lower (that is, the right figure) is superior in the $O_2$ discharge capacity because the collision frequency of the gas molecules is higher and accordingly $O_2$ molecules in the exhaust gas more easily collide with the surface of the pump electrode 31 to be removed. However, if the height on the entrance side is lowered, since an amount of the gas drawn into the chamber 2 decreases, the detection accuracy of $NO_x$ is lowered. On the other hand, in the case where the chamber height is higher (that is, the left drawing), although the $O_2$ discharge capacity is lowered, the detection accuracy can be expected to increase because the gas inflow rate increases.

Accordingly, in the present invention, as shown in FIGS. 4 and 6, the chamber height (that is, the cross-sectional area) is sufficiently large on the entrance side of the pump electrode 31 to ensure a gas flow amount, and is gradually decreased so that the $O_2$ discharge capacity increases toward the exit side. Further, the chamber height is set lower at the intermediate part where the pump electrode 31 is formed, particularly, at the center part to ensure a large space at both side end parts to thereby increase the gas diffusibility and increase the responsiveness. The deformed wall surface does not disturb the gas flow because it has a smooth curved shape. Since the gas flow is agitated because of increase of a flow velocity difference between the center part where the flow velocity is low and the side end part, the collision frequency between the gas and the pump electrode 31 increases, and the ambient gas is further drawn by the $O_2$ discharge, it is possible to remove $O_2$ efficiently. Preferably, the chamber 2 is formed such that the chamber height is minimum on the downstream side of the center part of the pump electrode 31, and more preferably, at the side end part on the exit side or in its vicinity, so that the space becomes gradually narrower in the gas flow direction and the $O_2$ pumping capacity increases as a result of which the $O_2$ concentration can be made approximately zero while passing through the pump cell. On the downstream of the exit side of the pump electrode 31, the chamber height (that is, the cross-sectional area) is made larger again to increase the gas diffusibility, and as a result, the exhaust gas from which $O_2$ has been discharged can be quickly introduced into the sensor cell 4 to achieve accurate detection with high responsiveness.

As described above, according to the present invention, since the shape of the ceramic sheet surface making the inner wall surface of the chamber 2 and the relationship between the height Hp of the diffusion layer 21 and the average height Have of the chamber 2 are specified depending on the position where the pump electrode 31 is formed, both the responsiveness and the detection accuracy can be achieved. FIG. 8 shows a relationship between the sensor characteristic by the gas sensor element 1 of the present invention and a deformation amount (that is, a warp amount) of the wall surface of the chamber 2, in which the gas discharge amount increases in proportion to the increase of the warp amount, and the gas responsiveness is approximately constant. For example, the warp amount represents, for the shape of the chamber 2 of the second embodiment shown in FIG. 9, the size of the warped shape of the surface of both the wall surfaces which are deformed to approach each other, and corresponds to the height Hm of the warped surface of the center part whose height is minimum of H2 whereas the height of both end parts is H2. As seen from the relationship of FIG. 8, the gas discharging efficiency increases with the increase of the deformation amount of the chamber 2. However, when the deformation amount of the chamber 2 is large, a fault is likely to occur during molding. Accordingly, preferably, the warped shape and the deformation amount are set appropriately within a predetermined warp amount range in which satisfactory formability can be ensured to obtain satisfactory gas discharging efficiency and gas responsiveness.

For example, in the shape of the chamber 2 of FIG. 9, the sensor characteristic is specified by the height of the chamber 2 (that is, the height H1 of both end parts and the height H2 of the center part). Accordingly, by setting the height of both end parts to ensure desired gas responsiveness and setting the height H2 of the center part from the upper limit value of the deformation amount, the gas discharging efficiency can be optimized. Alternatively, the height Hm of the warped surface of the opposite surfaces may be set by calculating a height difference ΔH (that is, the difference between the height H1 of both end parts and the height H2 of the center part) from the height H2 of the center part for obtaining desired gas discharging efficiency. The two wall surfaces may have the same warp amount. However, by setting the wall surface formed with the pump electrode 31 smaller, it is possible to suppress deformation of the pump electrode 31. Further, in a case where the wall surface formed with the pump electrode 31 is flat and only the opposite surface has a warped shape as the shape of the chamber 2 of the first embodiment shown in FIG. 10(*a*), it is easy to form the chamber 2 because the pump electrode 31 is less affected.

FIGS. 10(*b*) to 10(*g*) show another example of the shape of the chamber 2. In the present invention, a shape of the warped surface is not limited to the shape of the above embodiments as long as the chamber average height and the warp amount are within the specified ranges. Preferably, to increase the above effects, the cross-sectional area is smaller on the exit side than at the entrance side of the pump electrode 31 in the longitudinal direction, and the height is lower at the intermediate part where the pump electrode 31 is formed than at the side end part in the transverse direction. Further, for the warped shape of the wall surface of the chamber 2, as long as one surface has a warped shape which is convex toward the inside of the chamber 2, the other surface is not limited thereto. The wall surface where the pump electrode 31 is formed may be a shape which warps toward the outside of the chamber 2 as shown in FIG. 10(*b*) in the longitudinal and transverse directions. In this case, it is slightly deformed in the longitudinal or transverse direction following the deformation of the wall surface opposite to the pump electrode 31. As shown FIG. 10(*c*), the wall surface of the chamber 2 may have a warped waveform shape having concave and convex portions.

The deformed wall surface of the chamber 2 does not necessarily have to have a smooth curved shape. It may be a warped surface having inclination of a roughly V cross section as shown in FIGS. 10(*d*) and 10(*e*). In this case, the position at which the height in the longitudinal direction is minimum (that is, the V-shape position of the vertex point) needs to be at the exit side end part of the pump electrode 31 (FIG. 10(*e*)) or the exit side end part in its vicinity (FIG. 10(*d*)), and the height in the transverse direction is minimum needs to be at the center of the pump electrode 31 (FIG. 10(*e*)) or the center part in its vicinity (FIG. 10(*d*)). As shown in the drawing in the longitudinal direction of FIG. 10(*f*), the height of the chamber 2 may be made constant downstream of the exit position of the pump electrode 31. Here, the warped shape on the upstream side has a smooth curved surface. However, it may have an inclined surface as shown in FIG. 10*d* or 10(*e*). Likewise, as shown in the drawing in the transverse direction of FIG. 10(*f*), if the height of at least one of the side end parts of the chamber 2 is sufficiently higher than the height of the intermediate part where the pump electrode 31 is formed, the height of the other side end part may be comparable to the height of the intermediate part. FIG. 10(*g*) shows an example in which both wall surfaces of the chamber 2 are made a warped surface like in the second embodiment, the warped amount being changed. Here, the warp amount of the wall surface where the pump electrode 31 is formed is set smaller. For FIGS. 10(*a*) to 10(*g*), the chamber shapes in the longitudinal direction and the transverse direction may be combined with each other arbitrarily.

Figure 11A:
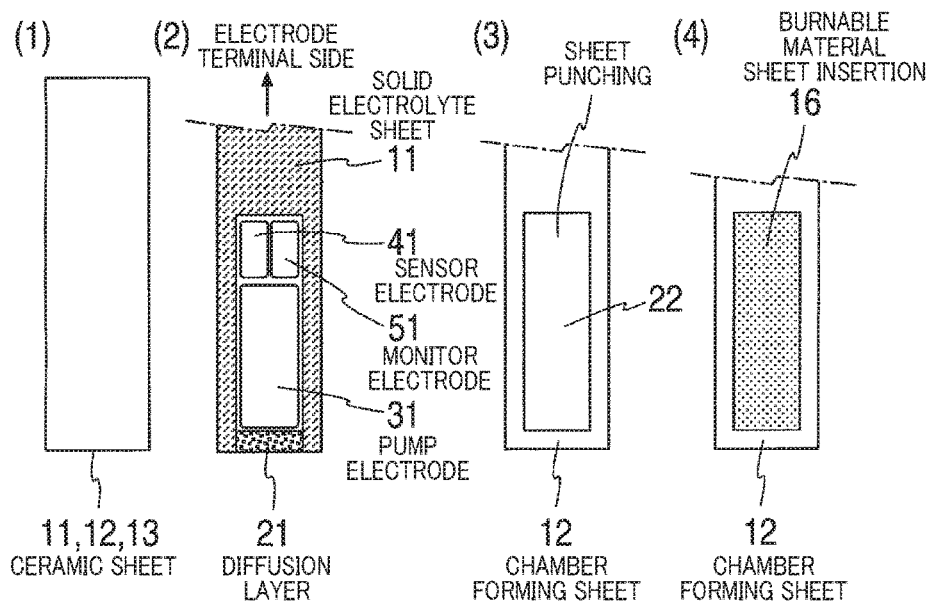
FIG. 11A is a process drawing for explaining a process of forming the chamber of the gas sensor element.

FIG. 11 shows an example of a manufacturing process of the gas sensor 1 having the shape of the chamber 2 of the present invention. In FIG. 11A, unsintered ceramic sheets for making the solid electrolyte sheet 11, the chamber forming sheet 12 and the shielding sheet 13 respectively are molded in step (1) at first. Next, in step (2), paste is printed at a predetermined position on the surface of the solid electrolyte sheet 11 where the pump electrode 31, the sensor electrode 41 and the monitor electrode 51 should be made. Further, not-shown paste for making leads for connection with not-shown electrode terminals is print-formed. In step (3), the chamber forming sheet 12 is punched at a predetermined position to form the opening 22 that makes the camber 2. Further, in step (4), a burnable material sheet 16 is inserted into the opening 22 of the chamber forming sheet 12.

The solid electrolyte sheet 11 is a mixed sheet of zirconia and organic matter, for example. The chamber forming sheet 12 and the shielding sheet 13 are made of a mixed sheet of alumina and organic matter, for example. The burnable material sheet 16 is a solo sheet or mixed sheet comprised of organic matter whose decomposition temperature is lower than or equal to 1000° C. For example, it includes a burnable material such as acrylic resin, PVB, fluoride resin or carbon so that the decomposition temperature becomes lower than or equal to 1000° C. The shape of the chamber 2 can be adjusted by adjusting the composition, thickness or shape of the burnable material sheet 16.

Figure 11B:
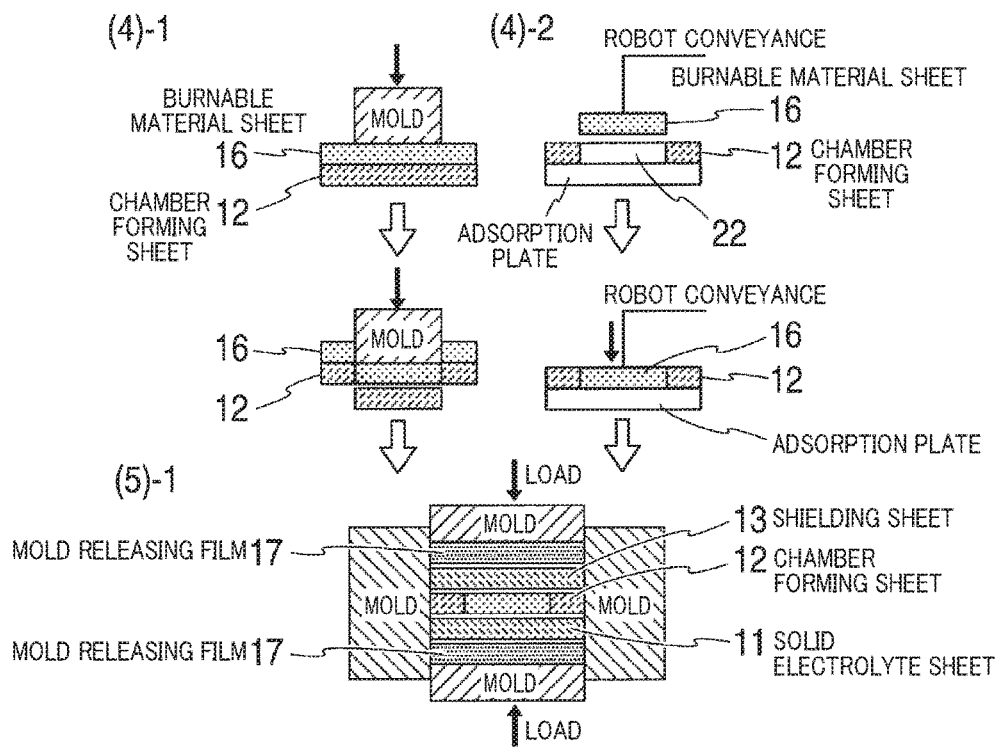
FIG. 11B is a process drawing for explaining the process of forming the chamber of the gas sensor element.
Figure 11C:
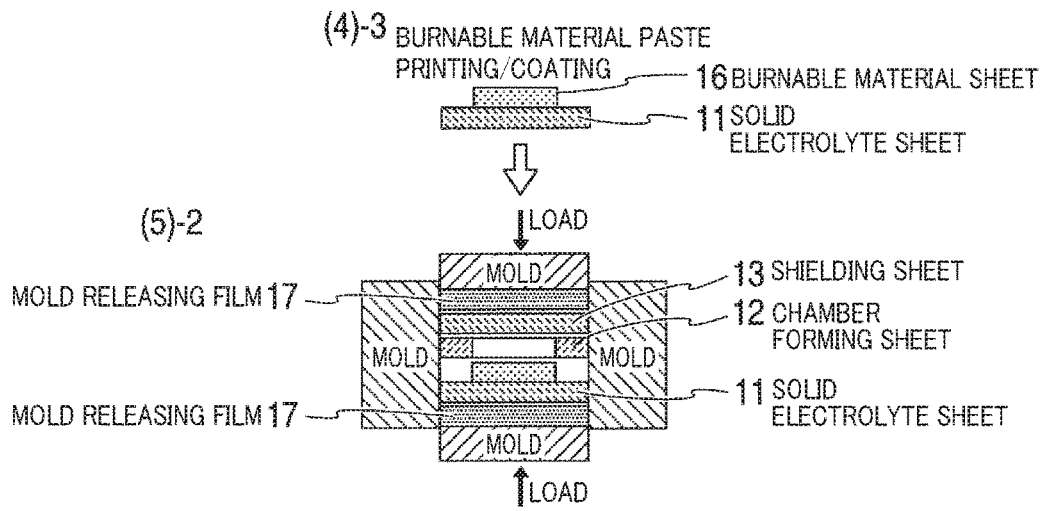
FIG. 11C is a process drawing for explaining the process of forming the chamber of the gas sensor element.

In FIG. 11B, step (4)-1 shows a specific example of a method of inserting the burnable material sheet 16 in which the burnable material sheet 16 is stacked on the chamber forming sheet 12, punched from above using a punching die having a shape corresponding to the chamber 2, and at the same time the punched burnable material sheet 16 is inserted into the punched hole of the chamber forming sheet 12. Alternatively, as shown in step (4)-2, it is possible that the chamber forming sheet 12 formed in advance in a predetermined shape is placed on an adsorption plate so that the burnable material sheet 16 formed in the predetermined shape can be robot-conveyed and inserted. Thereafter, in step (5)-1, the solid electrolyte sheet 11 is stacked with the chamber formation sheet 12 and the shielding sheet 13 on its top surface in this order, further a mold releasing film 17 being stacked upward and downward, and then is put in a mold.

This stacked body is applied with a load (15-50 MPa, for example) and compressed at a temperature (for example, 60 to 80° C.). As shown as step (4)-3 in FIG. 11C, it may be possible that the solid electrolyte sheet 11 is printed or coated with paste made of burnable material at a predetermined position on its top surface, stacked with the chamber forming sheet 12 punched in advance in a predetermined shape and the shielding sheet 13 in this order, and then disposed in a mold to make it possible to perform embedding and compression of the burnable material. Thereafter, in step (5)-2, a compressed body of the duct forming sheet 14 and the heater layer 6 manufactured by a known method is stacked and joined, and then sintered to make the gas sensor element 1.

Figure 12A:
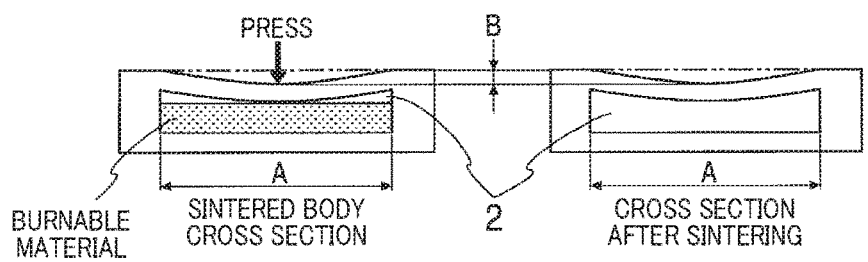
FIG. 12A is a schematic cross-sectional diagram for explaining a method of adjusting the chamber shape of the gas sensor element.

The shape of the chamber 2 of the obtained gas sensor element 1 can be controlled by the sheet thickness of the burnable material disposed in the chamber 2 before step (5)-1. For example, the left drawing of FIG. 12A schematically shows a case where one wall surface of the chamber 2 (that is, the top surface in the drawing) has a warped shape, in which an organic matter sheet whose principal component is resin or carbon is used as the burnable member whose thickness is adjusted in accordance with the warp amount in advance. At the time of the mold-pressing, the burnable member is housed excluding the upper end part of the chamber 2, and is depressed by applying a load from above to curve the wall surface facing the space of the chamber 2. At this time, since the deformation amount is small at the corner part of the chamber 2, a warped shape as described in the first embodiment can be formed relatively easily by appropriately adjusting the thickness of the burnable material relative to the distance A between both end parts. By sintering this, a hollow shape of the chamber 2 having a desired warp amount B can be made as shown in the right drawing of FIG. 12A.

To deform only one wall surface to be convex inwardly like the shape of the chamber 2 of FIG. 12A, it is possible to adopt 1: inserting a rubber film between a sheet to be deformed and the mold releasing film 17; 2: making the mold releasing film 17 on the side of a sheet to be deformed thick and making the mold releasing film 17 on the opposite side thin; and 3: making the mold releasing film 17 on the opposite side of a sheet to be deformed hard by pre-pressing. Further, it is possible to make the chamber 2 in a shape in which both the wall surfaces are convex inwardly as in the second embodiment by pressing from both sides with a space being left at both sides of the burnable material housed in the chamber 2.

Figure 12B:
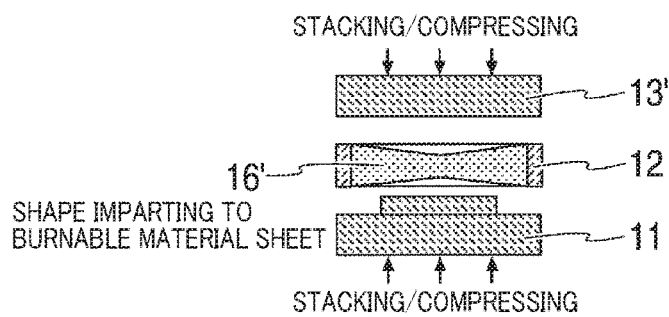
FIG. 12B is a schematic cross-sectional diagram for explaining another method of adjusting the chamber shape of the gas sensor element.

Alternatively, as shown in FIG. 12B, the burnable material sheet 16 may be provided with a desired warped shape at its surface prior to step (5)-1. In the drawing, an unsintered ceramic sheet 13 for making the shielding sheet 13 is disposed above the surface to be coated with electrode paste of the solid electrolyte sheet 11 (that is, the top surface in the drawing), and the chamber forming sheet 12 including the burnable material sheet 16 whose principal component is resin or carbon is disposed between them. At this time, by depressing the top and bottom surfaces of the burnable material sheet 16 in a mortar shape and deforming the surfaces of the shielding sheet 13 and the solid electrolyte sheet 11 which are in contact with theses surfaces, both the wall surfaces of the chamber 2 can be formed in a predetermined shape corresponding to the shape of the burnable material sheet 16. It is a matter of course that only one side of the burnable material sheet 16 may be depressed to deform only one corresponding surface.

Third Embodiment

Figure 13:
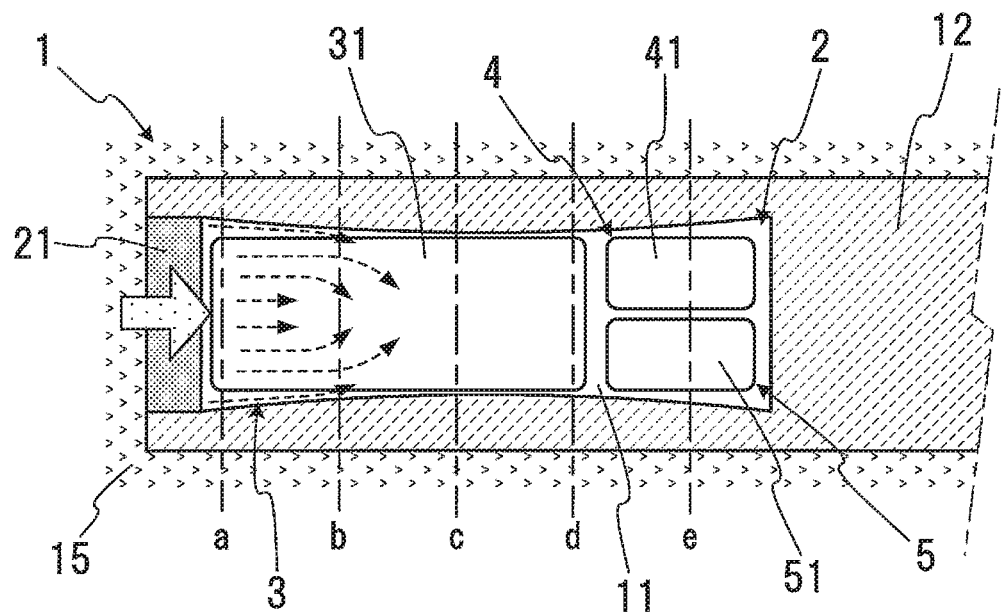
FIG. 13 is a diagram showing a planar structure of a distal end part of a gas sensor element of a third embodiment.
Figure 14:
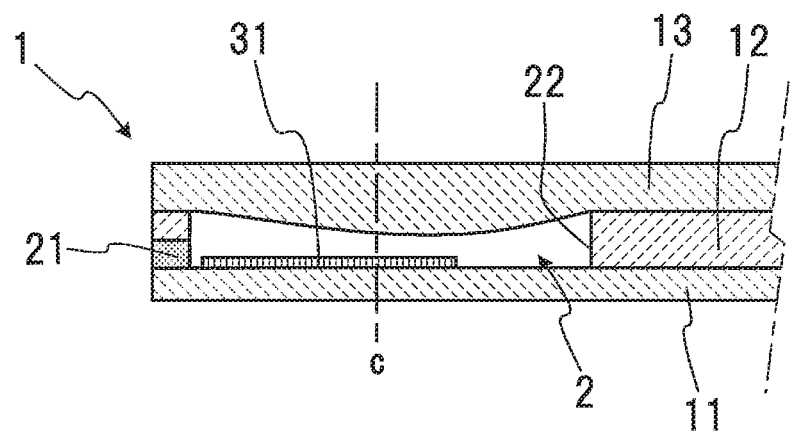
FIG. 14 is a longitudinal cross-sectional view schematically showing a chamber structure which is a main part of the gas sensor element.
Figure 15:
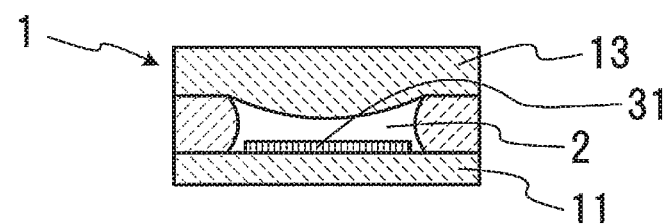
FIG. 15 is a transverse cross-sectional view schematically showing the chamber structure which is the main part of the gas sensor element.

As shown as a third embodiment in FIGS. 13 to 15, it is possible that, in addition to the wall surface opposite to the gas sensor element 1 in the stacking direction, at least one of the inner surfaces of the opening 22 of the chamber forming sheet 12 constituting the wall surface opposite to the gas sensor element in the transverse direction may be formed in a warped shape. The warped shape of the shielding sheet 13 making the chamber wall, the shape and disposition of the diffusion layer 21 and the relationship between the height Hp of the diffusion layer 21 and the average height Have if the chamber 2 at the position where the pump cell 3 is formed in this embodiment are the same as those in the first embodiment. In the following, explanation is given with a focus on differences with the first embodiment.

Specifically, as shown in FIGS. 13 and 14, the chamber forming sheet 12 is formed with the roughly rectangular opening 22 in the longitudinal cross section, and of the inner surfaces exposed to the chamber 2, both the pair of the inner surfaces extending in the longitudinal direction are formed in a warped surface having a chevron shape which is convex inwardly of the chamber 2. By these warped surfaces, the width of the chamber 2 gradually decreases from the entrance part a toward the exit part d of the pump electrode 31 at the position where the pump cell 3 is formed, and preferably, the warp amount becomes maximum at downstream of the center part of the pump electrode 31. In this case, it is preferable that the chamber widths Wa to We at the respective parts a to e within the chamber 2 satisfy the relationship of entrance width Wa>Wb>Wc≥exit width Wd. Like the first embodiment, the chamber heights Ha to He depending on the warped surface of the shielding sheet 13 are in the relation of entrance height Ha>Hb>Hc≥exit height Hd.

As shown in FIG. 15, the area of the transverse cross section of the chamber 2 becomes minimum at downstream of the center part of the pump electrode 31. The chamber 2 has a warped shape in which the surface of the shielding sheet 13 making the top wall and the pair of the surfaces of the chamber forming sheet 12 making the side walls are convex inwardly of the chamber 2, and each of them is formed in a chevron shape which is convex inwardly of the chamber 2 in which the warp amount becomes maximum at the center part. In the not-shown entrance part a, like the first embodiment, the chamber 2 has a roughly rectangular cross sectional shape in which the cross sectional area gradually increases toward the downstream side.

As shown by the arrows in FIG. 13, the gas introduced into the chamber 2 forms a flow heading to the center part of the pump cell 3 along the warped shape of the pair of the surfaces of the chamber forming sheet 12 that projects into the chamber 2. Further, it forms a flow heading to the pump electrode 31 on the solid electrolyte sheet 11 along the warped shape of the surface of the shielding sheet 13. Accordingly, the $O_2$ discharging capacity of the pump electrode 31 can be further increased. The chamber 2 includes a space at its four corners in the transverse direction, and accordingly the gas diffusibility is ensured.

The warp amount of the surface of the chamber forming sheet 12 can be set arbitrarily. Normally, when the warp amount is larger than or equal to 0.10%, the gas flow agitating effect can be obtained. Preferably, the maximum value of the warp amount is set such that the warped surface does not project inwardly of the chamber 2 beyond the peripheral edge part of the pump electrode 31. The maximum value of this warp amount depends on the shape of the chamber 2 or disposition of the pump electrode 31. For example, when the length of the chamber 2 is 14 mm, and the gap between the side wall of the chamber 2 and the peripheral edge part of the pump electrode 31 is 160 μm, the maximum value of the warp amount is 1.2%.

As described above, according to the shape of the chamber 2 of the third embodiment, it is possible to further promote the $O_2$ discharge by the pump electrode 31 by increasing the flow velocity difference of the gas flow while ensuring the responsiveness. Further, the warped shape of the surface of the chamber forming sheet 12 may be combined with the shape of the chamber 2 of the second embodiment.

EXAMPLES

To confirm the advantageous effects of the present invention, the gas sensor element 1 having the shape of FIG. 16 or 17 was manufactured while changing the height Hp of the diffusion layer 21, the shape of the chamber 2 and the shape of the pump cell 3 as shown in table 1 using the above described method as test elements and checked in terms of the sensor characteristics (practical examples 1 to 6). Further, test elements whose chamber shape or warped shape is out of the range of the present invention were manufactured for comparison purpose (comparative examples 1 to 5). As shown in the table in FIG. 16, the transverse length A of the sensor electrode 41 of the sensor cell 4: 1 mm, the longitudinal length B: 2 mm, the transverse length C of the chamber 2: 2.4 mm, the transverse length E of the pump electrode 31 of the pump cell 3: 2.1 mm are common to all the practical examples and all the comparative examples. For practical examples 1 to 6 and comparative examples 1 and 3-5, the longitudinal length D of the chamber 2 was set to 9 mm, and the longitudinal length B of the chamber 2 was set to 6.5 mm. In comparative example 2, the longitudinal length D of the chamber 2 was set longer to 14 mm, and the longitudinal length F of the pump electrode 31 of the pump cell 3 was set longer to 11 mm.

Figure 17A:
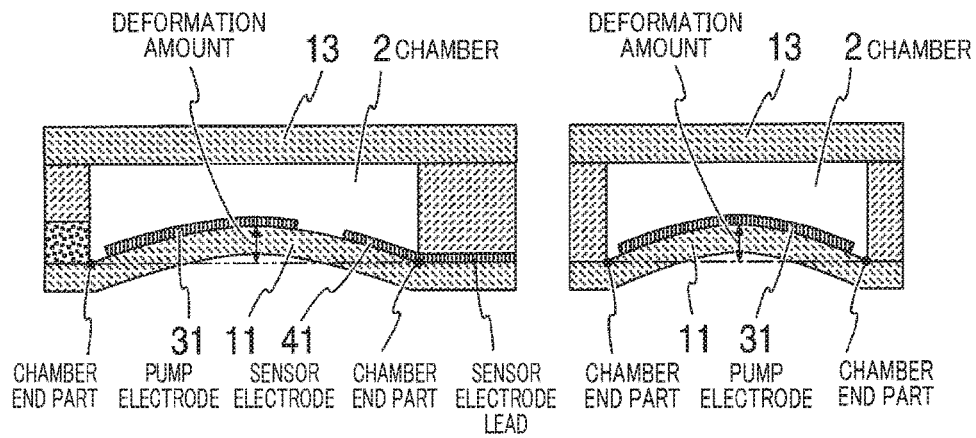
FIG. 17A is a schematic cross-sectional diagram for explaining a method of evaluating a warp amount in the practical examples.
Figure 17B:
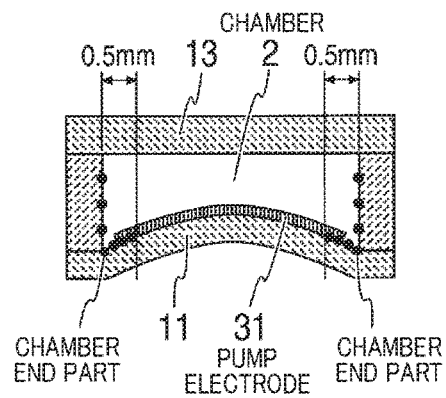
FIG. 17B is a schematic cross-sectional diagram for explaining a method of specifying the position of the chamber end part in evaluating the warp amount.

As shown in FIG. 17A and FIG. 17B, the test elements of practical examples 1 to 6 and comparative examples 1 and 3-5 are formed in a warped shape in which the solid electrolyte sheet 11 making the lower wall surface of the chamber 2 is recessed by applying a load from the outside so as to be curved and deformed upward, and the surface where the pump electrode 31 and the sensor electrode 41 are formed is curved so as to be convex to the inside of the chamber 2, that is, to the shielding sheet 13. Comparative examples 1 and 2 have a warped shape in which the solid electrolyte sheet 11 expands to the outside of the chamber 2. Table 1 shows results of measurements of the warped amount of these practical examples and comparative examples.

Evaluation of the warped amount was performed in the following manner. As shown in FIG. 17A, each obtained element sintered body was cut or polished vertically with respect to the longitudinal direction and the transverse direction, to make a chamber cross section. A maximum deformation amount was measured by connecting between the chamber end parts by a straight line through image observation for this chamber cross section. Further, the deformation amounts in the longitudinal direction and the transverse direction of the chamber 2 were converted into warp amounts (%) respectively, and a larger one of them was determined as a warped amount by comparing them.

The warped amount (%)=100×[chamber deformation amount (μm)/chamber end part-end part distance (μm)]

The chamber end part position was defined as shown in FIG. 17B. That is, three points are set arbitrarily in the chamber vertical direction, and an approximate line (a dotted line) is drawn on both sides of the chamber 2. Three points are set in a range of 0.5 mm from the approximate line in the vertical direction, and approximate lines (dotted lines) are drawn. Intersection points of these approximate lines were defined as the chamber end parts.

Figure 18:
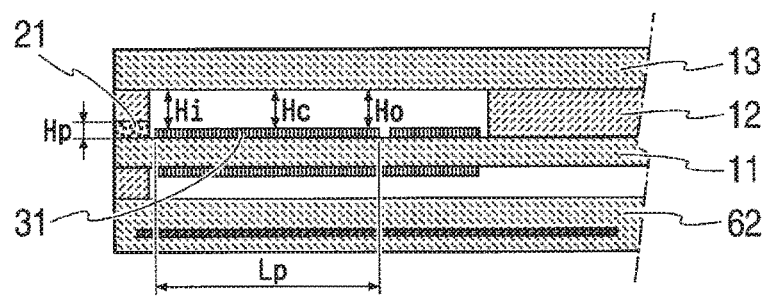
FIG. 18 is a schematic cross-sectional diagram for explaining a method of calculating a chamber average height in the practical examples.

Further, for each of the practical examples and the comparative examples, the height Hp in the stacking direction of the diffusion layer 21 and the average height Have of the chamber 2 at the position where the pump cell 3 is formed were measured to be shown in table 1. As shown in FIG. 18, the height between the solid electrolyte sheet 11 and the shielding sheet 13 was measured at each of the entrance part, center part and exit part of the pump electrode 31 in the gas flow direction, and an average value of them was obtained as the average height Have.

The average height $Have=(pump\ cell\ entrance\ height\ Hi+center\ height\ Hc+exit\ height\ Ho)/3$ In each of the practical examples 1 to 6, the height Hp of the diffusion layer 21 is lower than the average height Have of the chamber 2, and the center height Hc and the exit height Ho of the chamber 2 are lower than the entrance height Hi of the pump cell 3. In practical examples 1 and 2, the height of the pump cell 3 gradually decreases from the entrance toward the exit, or is the same at the center and the exit. In practical examples 3 to 6, the height is approximately the same at the center and the exit, or slightly higher at the center. In comparative example 5, the height Hp of the diffusion layer 21 is higher than the average height Have of the chamber 2.

Table 1 shows results of confirmation of the $O_2$ discharging capacity and gas responsiveness of practical examples 1 to 6 and comparative examples 1 to 5. For the $O_2$ discharging capacity, the symbol X represents that it was not possible to measure the NOx current value because the oxygen current value (background) of the monitor cell 5 was large and the differential current between sensor cell 4 and the monitor cell 5 was unstable, while the symbol ○ represents that it was possible to measure the NOx current value because the oxygen current value (background) of the monitor cell 5 was small and the differential current between sensor cell 4 and the monitor cell 5 was stable. For the gas responsiveness, the symbol X represents that the responsiveness with respective to variation of the NOx gas concentration was poor and unmeasurable, while the symbol ○ represents that the responsiveness with respective to variation of the NOx gas concentration was good and measurable.

Figure 19A:
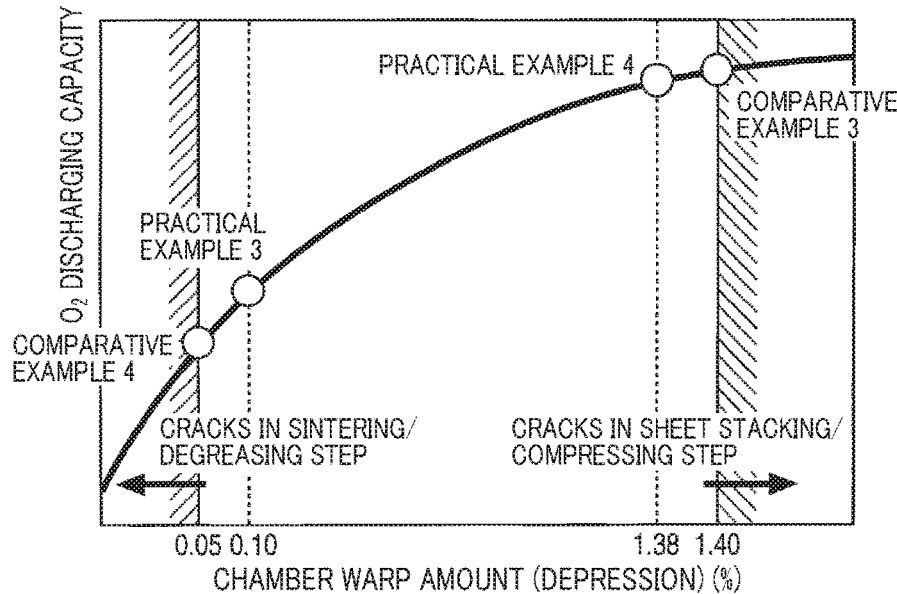
FIG. 19A is a diagram showing a relationship between the warp amount and the oxygen discharging capacity in the practical examples.

FIG. 19A shows the relationship between the chamber warp amount and the $O_2$ discharging capacity of the practical examples and comparative examples that have a chamber concaved shape.

Figure 19B:
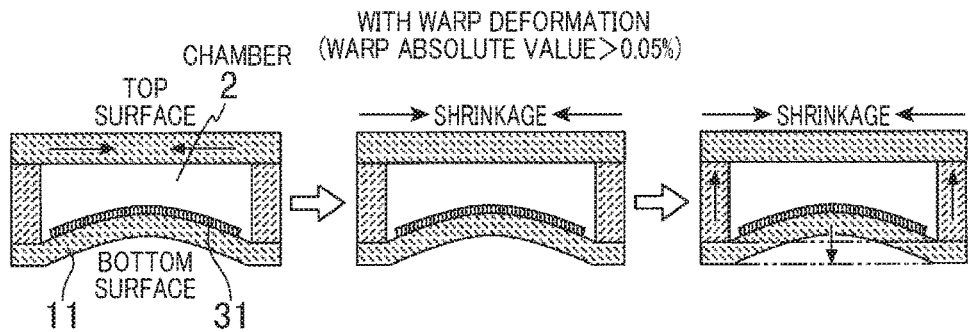
FIG. 19B is a schematic cross-sectional diagram for explaining a crack suppression effect depending on the warp amount in the practical examples.
Figure 19C:
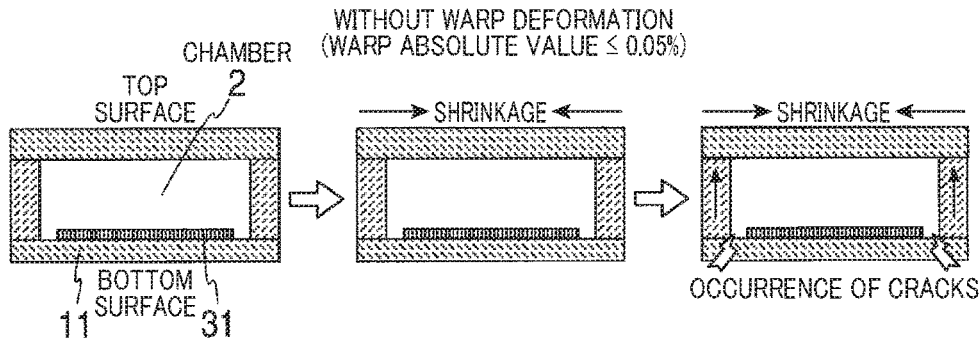
FIG. 19C is a schematic cross-sectional diagram for explaining a relationship between the warp amount and crack occurrence in comparative examples.

As apparent from FIG. 19A, the $O_2$ discharging capacity increases with the increase of the chamber warp amount. However, in comparative example 4 where the chamber warp amount is 1.40%, cracks occurred in the sheet stacking/compressing step. Also, in comparative example 3 where the chamber warp amount is 0.05%, cracks occurred in the sintering/degreasing step. It was found that satisfactory results cannot be obtained if the chamber warp amount is too large or too small. FIGS. 19B and 19C show comparison of behavior in the sintering/degreasing step between a case where the chamber warp amount exceeds 0.05% and a case where the chamber warp amount does not exceed 0.05%. For example, if a degrease shrinkage occurs first due to variation of the degreasing temperature or resin extraction, since there is no allowance for elongation, a tensile stress occurs and cracks occur easily (For example, see FIG. 19C).

Whereas, by making the solid electrolyte sheet 11 in a warped shape on the bottom surface side and causing it to be extensionally deformed in advance, cracks can be prevented by lessening the tensile stress during degreasing (for example, see FIG. 19B).

On the other hand, in practical example 3 where it is 0.10% and practical example where it is 1.38%, no cracks occurred. Accordingly, the chamber warp amount is set preferably higher than or equal to 0.10% and lower than or equal to 1.38% in the present invention. As apparent from the results in table 1, according to practical examples 1 to 6, satisfactory results in both the $O_2$ discharging capacity and the gas responsiveness were obtained. On the other hand, in comparative example 1 where the chamber 2 is deformed to expand to the outside and comparative example 5 where the height Hp of the diffusion layer 21 is higher than the average height Have, the $O_2$ discharging capacity is insufficient. In comparative example 2 where the chamber 2 is deformed to expand to the outside, the $O_2$ discharging capacity is improved by lengthening the longitudinal lengths of the chamber 2 and the pump cell 3, however, the gas responsiveness is lowered.

TABLE 1

| | DIFFUSION LAYER HEIGHT Hp μm | CHAMBER HEIGHT | | | | PUMP CELL LENGTH Lp mm |
|---|---|---|---|---|---|---|
| | | AVERAGE Have μm | PUMP CELL ENTRANCE HEIGHT Hi μm | PUMP CELL CENTER HEIGHT Hc μm | PUMP CELL EXIT HEIGHT Ho μm | |
| COMPARATIVE EXAMPLE 1 | 101 | 201 | 199 | 203 | 201 | 6.5 |
| COMPARATIVE EXAMPLE 2 | 101 | 200 | 198 | 201 | 201 | 11 |
| COMPARATIVE EXAMPLE 3 | 100 | 182 | 200 | 170 | 175 | 6.5 |
| COMPARATIVE EXAMPLE 4 | 100 | 200 | 200 | 199 | 200 | 6.5 |
| COMPARATIVE EXAMPLE 5 | 198 | 191 | 201 | 191 | 182 | 6.5 |
| PRACTICAL EXAMPLE 1 | 101 | 191 | 202 | 190 | 182 | 6.5 |
| PRACTICAL EXAMPLE 2 | 101 | 190 | 201 | 185 | 185 | 6.5 |
| PRACTICAL EXAMPLE 3 | 100 | 199 | 200 | 198 | 199 | 6.5 |

TABLE 1-continued

| | | | | | | | |
|---|---|---|---|---|---|---|---|
| PRACTICAL EXAMPLE 4 | 100 | 183 | 201 | 172 | 175 | 6.5 | |
| PRACTICAL EXAMPLE 5 | 160 | 184 | 200 | 175 | 177 | 6.5 | |
| PRACTICAL EXAMPLE 6 | 10 | 14 | 15 | 12 | 15 | 6.5 | |

| | CHAMBER CRACKS | CHAMBER WARPED SHAPE | CHAMBER WARP AMOUNT % | $O_2$ DISCHARGE | GAS RESPONSIVENESS |
|---|---|---|---|---|---|
| COMPARATIVE EXAMPLE 1 | ABSENT | EXPANSION | 0.20 | x | ○ |
| COMPARATIVE EXAMPLE 2 | ABSENT | EXPANSION | 0.15 | ○ | x |
| COMPARATIVE EXAMPLE 3 | PRESENT | DEPRESSION | 1.40 | UNMEASUREABLE | UNMEASUREABLE |
| COMPARATIVE EXAMPLE 4 | PRESENT | DEPRESSION | 0.05 | UNMEASUREABLE | UNMEASUREABLE |
| COMPARATIVE EXAMPLE 5 | ABSENT | DEPRESSION | 0.60 | x | ○ |
| PRACTICAL EXAMPLE 1 | ABSENT | DEPRESSION | 0.60 | ○ | ○ |
| PRACTICAL EXAMPLE 2 | ABSENT | DEPRESSION | 1.00 | ○ | ○ |
| PRACTICAL EXAMPLE 3 | ABSENT | DEPRESSION | 0.10 | ○ | ○ |
| PRACTICAL EXAMPLE 4 | ABSENT | DEPRESSION | 1.38 | ○ | ○ |
| PRACTICAL EXAMPLE 5 | ABSENT | DEPRESSION | 1.19 | ○ | ○ |
| PRACTICAL EXAMPLE 6 | ABSENT | DEPRESSION | 0.14 | ○ | ○ |

In the present invention, the gas sensor 1 at least needs to have the structure in which the pump cell 3 and the sensor cell 4 are disposed from the upstream side within the chamber. By adopting the shape of the chamber 2 of the present invention without being limited to the stacked structure of the above described embodiments, the same advantages can be expected. The wall surface of the chamber 2 may be other than the above described shapes. As methods of manufacturing the gas sensor element 1, various methods for forming the shape of the chamber 2 of the present invention other than the methods described in the above embodiments can be adopted.

INDUSTRIAL APPLICABILITY

As described above, according to the present invention, a gas sensor that satisfies both the detection accuracy and responsiveness can be implemented. This gas sensor is suitable as a $NO_x$ gas sensor to be installed in an exhaust system of an internal combustion engine to contribute to increase of the exhaust purification performance. The specific gas component to be detected by the gas sensor of the present invention is not limited to $NO_x$. For example, it may be $SO_x$ or others. The measurement gas is not limited to an exhaust gas from an internal combustion engine. It can be used for detecting a specific gas in various gases to exhibit excellent sensor characteristics.

REFERENCE SIGNS LIST

1 gas sensor element
11 solid electrolyte sheet (first ceramic sheet)
12 chamber forming sheet (second ceramic sheet)
13 shielding sheet (third ceramic sheet)
2 chamber
21 diffusion layer
3 pump cell
31 pump electrode
4 sensor cell
41 sensor electrode

The invention claimed is:

1. A gas sensor for detecting a specific component in a measurement gas, comprising
   a chamber that is provided in a gas sensor element comprised of stacked tabular ceramic sheets comprised of first, second and third ceramic sheets, the measurement gas being introduced into the chamber through a porous diffusion layer provided at an end part thereof in a longitudinal direction of the gas sensor element;
   a pump cell that has a pump electrode disposed on an upstream side of a gas flow within the chamber for pumping out oxygen in the measurement gas; and
   a sensor cell that has a sensor electrode disposed on a downstream side of the gas flow within the chamber for detecting a concentration of a specific gas in the measurement gas whose oxygen concentration has been reduced, wherein
   the gas sensor element has a structure in which the first ceramic sheet on whose surface facing the chamber the pump electrode and the sensor electrode are disposed, the second ceramic sheet having an opening to make the chamber, and the third ceramic sheet covering the opening to define the chamber are stacked on one another,
   the chamber has a warp sharp in which a surface of at least one of the first ceramic sheet and the third ceramic sheet constituting a chamber wall is convex inwardly of the chamber at a position where the pump cell is formed, a warp amount of the surface being set in a range from 0.1% or high to 1.38% or lower, the diffusion layer and the chamber satisfy a relationship of Hp<Have, where Hp is a height of the diffusion layer in a stacking direction and Have is an average height of the chamber in a stacking direction at the position where the pump cell is formed, and if the surface of at least one of the first and third ceramic sheets without warping is defined as a reference surface, the warp amount of the surface at least one of the first and third sheets is calculated based on a maximum deformation amount of the surface of at least one of the first and third ceramic sheets relative to the reference surface in a vertical cross-section, the vertical cross section being perpendicular to the longitudinal direction and a transverse direction of the gas sensor element.

2. The gas sensor according to claim 1, wherein the longitudinal direction of the gas sensor element is a gas flow direction, and the chamber has such a shape that a cross-sectional area thereof at a gas entrance part is smaller than a cross-sectional area thereof at a gas exit part, and a height at a position of a center part of the pump electrode is lower than a height of at least one wall surface of an end part of the chamber, the diffusion layer being disposed along the gas entrance part of the pump electrode.

3. The gas sensor according to claim 1, wherein the chamber has such a shape that a cross-sectional area thereof gradually decreases from a gas entrance part toward a gas exit part of the pump electrode in the longitudinal direction of the gas sensor element, and becomes minimum at downstream of a center part in a gas flow direction.

4. The gas sensor according to claim 1, wherein the chamber has such a shape that a height thereof gradually decreases from one of or both of end parts of the chamber toward a position of a center part of the pump electrode in a transverse direction of the gas sensor element.

5. The gas sensor according to claim 1, wherein the chamber has a warped shape in which at least one of inner surfaces of the opening of the second ceramic sheet that constitute chamber walls opposite in a transverse direction of the gas sensor element is convex inwardly of the chamber at the position where the pump cell is formed.

6. The gas sensor according to claim 1, wherein the first ceramic sheet is a solid electrolyte sheet having oxygen ion conductivity, and includes a reference electrode corresponding to the pump electrode or the sensor electrode on a surface thereof opposite to the chamber to constitute the pump cell or the sensor cell.

7. The gas sensor according to claim 1, wherein the second ceramic sheet and the third ceramic sheet are insulation sheets having no permeability to the measurement gas.

8. The gas sensor according to claim 1, wherein the measurement gas is an exhaust gas of an internal combustion engine, and the specific gas component is a nitrogen oxide gas.

* * * * *